United States Patent [19]

Bliss

[11] 4,228,163

[45] Oct. 14, 1980

[54] METHOD FOR TREATING PSEUDOFOLLICULITIS BARBAE

[75] Inventor: William E. Bliss, Fort Washington, Pa.

[73] Assignee: Dermik Laboratories, Fort Washington, Pa.

[21] Appl. No.: 25,390

[22] Filed: Mar. 30, 1979

[51] Int. Cl.$^3$ ...................... A61K 31/56; A61K 31/47
[52] U.S. Cl. .................................... 424/240; 424/258; 424/338
[58] Field of Search ....................... 424/258, 338, 240

[56] References Cited

U.S. PATENT DOCUMENTS 3,535,422  10/1970  Cox et al. .............................. 424/164

OTHER PUBLICATIONS

The Merck Manual, 10th ed., 1961, pp. 1440–1441.
The Merck Index, 9th ed., 1976, p. 276 (2147).
Chemical Abstracts, 84:126758f, (1976).

*Primary Examiner*—Leonard Schenkman
*Attorney, Agent, or Firm*—Miller & Prestia

[57] ABSTRACT

The present invention relates to a method of treating pseudofolliculitis barbae in humans by topically administering to a person in need of such treatment an effective amount of the synergistic combination of benzoyl peroxide and chlorohydroxyquinoline, and the compositions therefor.

8 Claims, No Drawings

METHOD FOR TREATING PSEUDOFOLLICULITIS BARBAE

SUMMARY OF THE INVENTION

This invention relates to the treatment of skin conditions such as pseudofolliculitis barbae and to compositions which have been found to be effective when topically applied to improve and heal said skin conditions in humans.

BACKGROUND OF THE INVENTION

Pseudofolliculitis barbae, which is commonly known as "razor bumps", is a condition of the skin in which hair tends to ingrow. The consequence is a foreign body type of inflammatory papule or pustule which in turn may progress into a large nodule or abscess. In general, pseudofolliculitis barbae is treated by topically applying a therapeutic agent to the infected area. Also, systemic antibiotics are utilized in severe cases when secondary infection has intervened. While some of the prior art therapeutic agents do provide some relief by treating the inflammation and infection, they have little effect with regard to the treatment or prevention of pseudofolliculitis barbae.

The prior art remedies for treating folliculitis, which is a superficial or deep infection of hair follicules, and sycosis barbae, which is a term used to describe a deep-seated folliculitis of the beard area, are only of use in the treatment of the secondary infections accompanying pseudofolliculitis barbae. The prior art remedies cannot prevent or be used in the treatment of pseudofolliculitis barbae.

It has now been discovered that skin conditions such as pseudofolliculitis barbae, as well as the inflammatory conditions and infections resulting therefrom, may be successfully treated as well as prevented from occurring.

DESCRIPTION AND PREFERRED EMBODIMENTS

The present invention relates to the topical treatment of skin conditions such as pseudofolliculitis barbae with the synergistic combination of benzoyl peroxide and chlorohydroxyquinoline.

Chlorohydroxyquinoline is a well known, commercially available compound which possesses anti-bacterial and anti-fungal activity. The preferred compound used in connection with the present invention is 5-chloro-8-hydroxyquinoline.

It is well known in the pharmacological arts that non-toxic acid addition salts of pharmacologically active amine compounds do not differ in activities from their free base. Thus, the term "chlorohydroxyquinoline" is meant to include those non-toxic acid addition salts which may be prepared by conventional methods from inorganic, higher fatty acids, high molecular weight acids, etc., and include such acids as:

| | |
|---|---|
| hydrochloric acid | succinic acid |
| hydrobromic acid | glycolic acid |
| sulfuric acid | lactic acid |
| nitric acid | salicyclic acid |
| phosphoric acid | benzoic acid |
| methane sulfonic acid | nicotinic acid |
| benzene sulfonic acid | phthalic acid |
| acetic acid | stearic acid |
| propionic acid | oleic acid |
| malic acid | abietic acid |

Benzoyl peroxide is a well known chemical represented by the structural formula:

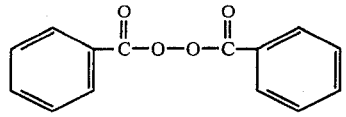

It is a colorless, odorless, tasteless, crystalline solid which is stable at ordinary room temperature but which is flammable and capable of exploding when confined and subject to grinding, heat or flame. Benzyol peroxide is a powerful oxidizing agent, and is often used in polymer chemistry as a free-radical generating catalyst. Recently it has been used as a keratolytic and anti-bacterial agent in the treatment of acne and seborrhea in humans. In this respect, attention is particularly invited to U.S. Pat. Nos. 3,535,422 and 3,530,217.

It has been surprisingly discovered herein that the combination of benzoyl peroxide and chlorohydroxyquinoline is an overwhelmingly effective therapeutic agent for the treatment of pseudofolliculitis barbae. More particularly, the combination of benzoyl peroxide and chlorohydroxyquinoline has been found to be especially effective in the treatment and management of pseudofolliculitis barbae and its associated symptoms of inflammation and infection.

The combination of benzoyl peroxide and chlorohydroxyquinoline has been known to be effective in the treatment of bacterial infections in humans. Thus, bacterial infections which may be secondary to the underlying folliculitis and are caused by bacteria, such as staphylococcus aureaus, and other gram positive organisms are among the skin infections contemplated to be treated by the process herein.

Moreover, it has been found that not only does the combination of chlorohydroxyquinoline and benzoyl peroxide provide a complete remission of the condition, it does not cause any deleterious side effects and, in addition, possesses desirable anti-inflammatory qualities.

In accordance with the process of the present invention, the benzoyl peroxide is generally advantageously incorporated in a suitable inert carrier, and the resultant composition is admixed with the chlorohydroxyquinoline prior to application to the area to be treated. By "inert", it is intended to mean carrier materials which do not chemically react with the benzoyl peroxide at ambient temperature and pressure.

The compositions used in the practice of the present process are made by any conventional means. Preferably, the benzoyl peroxide is admixed with chlorohydroxyquinoline just prior to the application to the skin for either the active treatment and prevention or prophylactic treatment of pseudofolliculitis barbae. Aqueous and alcoholic solutions of these compounds are useful, as are cosmetic preparations containing them, whether based on aqueous or lipophilic media or a combination of both such phases. For example, the present combination may be used in cosmetics, including liquid, solid and semi-solid paste, cream or gelatinous preparations. The preparations may contain the active ingredients in an amount from about 0.05 to about 20% by weight of the total formulation in which the active ingredients are incorporated and conventionally applied. Preferably, the chlorohydroxyquinoline is utilized in the composition in the amount of 0.4 to about 35% by weight of benzoyl peroxide in the composition, preferably 0.5 to about 5% by weight of benzoyl peroxide present.

In accordance with the process of the present invention, the benzoyl peroxide is generally advantageously incorporated in a suitable inert carrier, and the resultant composition is admixed with a composition containing the chlorohydroxyquinoline shortly prior to topically applying it to the infected area. The administration is performed one to two times daily until complete remission occurs.

The suitable inert carrier materials useful in the formulation of the therapeutic compositions used in the practice of this invention include any of those ingredients used in the preparation of alcohol or acetone gels, creams, ointments, lotions, and the like. Preferably, the benzoyl peroxide is admixed with a dry non-liquid crystalline carrier such as calcium phosphate, talc, diatomaceous earth, calcium silicate, starch, polyhydric alcohols such as dextrin, dextran, etc., and the like.

The chlorohydroxyquinoline, prior to admixing with the benzoyl peroxide, may be incorporated into the cosmetic vehicle. Usually, the cosmetic vehicle will contain from 1 to 100% of an aqueous or an oily phase of a solid material, and sometimes, as in the case of emulsions, will contain both aqueous and oily phases, often with a surface-active material to aid in the emulsification. Such surface-active agents may be anionic, non-ionic, cationic or amphoteric. If the medium is lipophilic, there will usually be present from 50 to 99% of oil, such as mineral oil, lanolin, lanolin derivatives of other lipophilic materials, together with the chlorohydroxyquinoline. The solvent, e.g. a lower alkanol such as ethanol or isopropanol, may also be used to thin the lipophilic phase to make it easier to apply. If the preparation is hydrophilic, it will usually contain from 50 to 99% of water, sometimes from 5 to 40% lower alkanol, polyhydric alcohol, glycol, and the like.

In addition, the therapeutic composition of this invention may include one or more steroidal compounds, such as, dexamethasone or hydrocortisone and its derivatives, in the chlorohydroxyquinoline preparation as described above. The steroid may be effective against unrelated or related skin conditions. If a steroid is added as an additional ingredient, it is preferred that the concentration of this steroid be up to 2% by weight of the total composition.

The following Examples are illustrative of formulations of compositions according to this invention but are not to be considered as limiting the scope of this invention.

EXAMPLE 1

A. Benzoyl peroxide (35 mg.) is thoroughly admixed with calcium phosphate (65 mg.) and placed in a vial.

B. Chlorohydroxyquinoline (0.25 mg.) is dissolved in 2 ml. of water-glycol (40:60). Methyl paraben (0.05 mg.) and propyl paraben (0.05 mg.) are then added as a preservative; the mixture is stored in a second vial.

For the treatment of pseudofolliculitis barbae, the composition of (A) is admixed with the composition of (B), and the resultant mixture is applied to the treatment area one to two times daily.

If desired, hydrocortisone or its derivatives may be added to the composition in the amount of 0.5% by weight of the composition for treatment of secondary infections.

EXAMPLE 2

An ointment is prepared as follows:

Chlorohydroxyquinoline (0.30 mg.) is dissolved in 2 ml. of water and 3 ml. of propylene glycol. Benzoyl peroxide (35.0 mg.) is added to the solution and the mixture is stirred with USP hydrophilic ointment (5.0 g.). The ointment thus prepared is then applied to the affected area for the treatment of pseudofolliculitis barbae.

If desired, hydrocortisone acetate in the amount of 0.25% by weight of composition may be added.

EXAMPLE 3

A lotion is prepared as follows:

Benzoyl peroxide (490.0 mg.) is admixed with 9.3 g. of an oil-in-water lotion prepared from mineral oil, cottonseed oil, isopropyl palmitate and water with a surfactant such as sorbitan sesquioleate. The ingredients in said oil-in-water lotion are present, for example, in 10:10:5:70:5 parts by weight, respectively. Chlorohydroxyquinoline (24.5 mg.) is added to the lotion and the mixture is applied to infected skin areas.

If desired, dexamethasone in the amount of 0.25% by weight of total composition may be added.

I claim:

1. A method for treating pseudofolliculitis barbae in humans and the prophylactic treatment thereof, which comprises: topically applying to involved areas of the human body an effective amount of a composition of benzoyl peroxide and 5-chloro-8-hydroxyquinoline in a concentration of about 0.05 to about 20% by weight of the total composition, in a suitable pharmaceutically acceptable carrier.

2. The method of claim 1 wherein chlorohydroxyquinoline is present in an amount of 0.4 to about 35% by weight of benzoyl peroxide.

3. The method of claim 2 wherein chlorohydroxyquinoline is present in an amount of 0.5 to about 5% by weight of benzoyl peroxide present.

4. The method of claim 1 wherein benzoyl peroxide is in a carrier comprising a dry crystalline water-soluble carrier and said chlorohydroxyquinoline is in a carrier comprising water and a glycol.

5. The method of claim 4 wherein said dry crystalline carrier is calcium phosphate.

6. The method of claim 4 wherein said dry crystalline carrier is starch.

7. The method of claim 1 including in said composition a steroid selected from the group consisting of dexamethasone and hydrocortisone or its derivatives in a concentration of 0–2% by weight of composition.

8. The method of claim 1 wherein said carrier is hydrophilic.